US010883973B2

(12) United States Patent
Manley

(10) Patent No.: US 10,883,973 B2
(45) Date of Patent: Jan. 5, 2021

(54) FUSE FOR DETECTING FAILURE OF GAS TRAP

(71) Applicant: BL Technologies, Inc., Minnetonka, MN (US)

(72) Inventor: Jesse Colin Manley, Boulder, CO (US)

(73) Assignee: BL TECHNOLOGIES, INC., Minnetonka, MN (US)

(*) Notice: Subject to any disclaimer, the term of this patent is extended or adjusted under 35 U.S.C. 154(b) by 412 days.

(21) Appl. No.: 15/312,498

(22) PCT Filed: Mar. 4, 2015

(86) PCT No.: PCT/US2015/018707
§ 371 (c)(1),
(2) Date: Nov. 18, 2016

(87) PCT Pub. No.: WO2015/178998
PCT Pub. Date: Nov. 26, 2015

(65) Prior Publication Data
US 2017/0089877 A1 Mar. 30, 2017

Related U.S. Application Data

(60) Provisional application No. 62/002,386, filed on May 23, 2014.

(51) Int. Cl.
G01N 33/00 (2006.01)
G01N 33/18 (2006.01)
G01N 27/12 (2006.01)
G01N 31/00 (2006.01)

(52) U.S. Cl.
CPC ......... G01N 33/0052 (2013.01); G01N 27/12 (2013.01); G01N 27/125 (2013.01); G01N 31/005 (2013.01); G01N 33/1846 (2013.01)

(58) Field of Classification Search
CPC .... G01N 27/12; G01N 31/005; G01N 27/125; G01N 33/1846; G01N 33/0052
See application file for complete search history.

(56) References Cited

U.S. PATENT DOCUMENTS

| 5,466,605 A | * | 11/1995 | Glaunsinger | C23C 8/10 436/101 |
| 5,635,729 A | | 6/1997 | Griessen et al. | |
| 6,007,777 A | | 12/1999 | Purcell et al. | |
| 6,143,568 A | | 11/2000 | Pilz | |
| 2004/0063215 A1 | | 4/2004 | Horiuchi et al. | |

FOREIGN PATENT DOCUMENTS

| GB | 2453970 A | 4/2009 |
| JP | 2005214766 A | 8/2005 |

(Continued)

OTHER PUBLICATIONS

Chinese Patent Application No. CN201580026878.5, Office Action dated Jun. 24, 2019.

(Continued)

Primary Examiner — Shogo Sasaki

(57) ABSTRACT

A gas detection fuse is provided, comprising a thin strip or sheet of a conductive material, such as a metal, connecting two electrodes for detecting a gas of interest. The metal is selected to be reactive with the gas of interest, and has a relatively large surface area, such that when the gas of interest contacts the metal, the electrical connection between the electrodes is broken (e.g., due to the metal losing physical integrity, or becoming non-conductive, as a result of the reaction with the gas). The gas of interest may be chlorine, and the conducting material may be tin. When the tin is exposed to chlorine the tin becomes oxidized to produce liquid tin tetrachloride, thus breaking the electrical connection.

12 Claims, 3 Drawing Sheets

(56) References Cited

FOREIGN PATENT DOCUMENTS

| JP | 2007178377 A | 7/2007 |
|----|--------------|--------|
| JP | 2008058253 A | 3/2008 |
| JP | 3162656 U | 9/2010 |
| JP | 2013137220 A | 7/2013 |
| TW | 201222612 A | 6/2012 |
| WO | 03029801 A1 | 4/2003 |

OTHER PUBLICATIONS

International Patent Application No. PCT/US2015/018707, International Preliminary Report on Patentability dated Dec. 8, 2016.
International Patent Application No. PCT/US2015/018707, International Search Report and Written Opinion dated Nov. 3, 2015.
Japanese Patent Application No. JP2016-567918, Office Action dated Apr. 9, 2019.
Mabrook et al., "An Inkjet-Printed Chemical Fuse," Applied Physics Letters, Dec. 2004, vol. 86 (1), pp. 013507-1-013507-3.
Taiwan Patent Application No. 104115382, Office Action dated May 1, 2019.
Lodewyckx, Peter et al. "Using the modified Wheeler-Jonas equation to describe the adsorption of inorganic molecules: chlorine", Carbon 41 (2003) 1215-1219.
Japanese Patent Application No. JP2016-567918, Office Action dated Oct. 29, 2019—English Translation Available.
Chinese Patent Application No. 201580026878.5, Office Action dated Jan. 2, 2020—English Translation Available.
Japanese Patent Application No. JP2016-567918, Office Action dated Jul. 21, 2020.

* cited by examiner

FUSE FOR DETECTING FAILURE OF GAS TRAP

FIELD

The present disclosure relates generally to detection of hazardous gasses. More particularly, the present disclosure relates to apparatus for detecting the presence of chlorine gas escaping a halogen trap.

BACKGROUND

A sample analyzer such as a total organic carbon (TOC) analyzer can sometimes produce hazardous gasses, depending on the sample being analyzed. In particular, chlorine gas produced when samples containing chlorides are analyzed is highly corrosive and could potentially result in personal injury and equipment failure in the field. Some TOC analyzers, including the InnovOx™ TOC analyzers from GE Analytical Instruments, include halogen traps. For example, activated carbon in a halogen trap can adsorb between 20%-50% of its mas in chlorine (P. Lodewyckx and L. Verhoeven, *Using the modified Wheeler-Jonas equation to describe the adsorption of inorganic molecules: chlorine*, Jan. 25, 2003. Pg: 1217-1219). However, once the reaction sites of the activated carbon have been used (i.e. the trap is saturated), or if the trap fails in some way, chlorine or other halogens can escape the trap. Typical commercially available gas sensors for measuring chlorine tend to be relatively complex and expensive. The inventor has determined a need for alternative means for detection of hazardous gasses such as chlorine.

SUMMARY

The present disclosure provides a gas detection fuse comprising a connecting member (e.g. a thin strip or sheet, one or more wires, etc.) comprising conducting material, such as a metal, connecting two electrodes for detecting a gas of interest. The conducting material is selected to be reactive with the gas of interest, and has a relatively large surface area, such that when the gas of interest contacts the conducting material, the electrical connection between the electrodes is broken (e.g., due to the conducting material losing physical integrity, or becoming non-conductive, as a result of the reaction with the gas).

The specification describes examples wherein the gas of interest is chlorine, and the metal is tin. When the tin is exposed to chlorine the tin becomes oxidized to produce liquid tin tetrachloride $(Sn(s)+2\ Cl2(g)\text{-} \text{-} ->SnCl4(l))$, thus breaking the electrical connection.

The fuse may be positioned at the outlet of a halogen trap of a TOC analyzer and operatively connected to a controller of the TOC analyzer. The fuse may thus be configured to act as a failsafe by triggering shut down of the TOC analyzer to halt further chlorine production when the electrical connection in the fuse is broken.

Fuses may be placed at strategic places in an installation or instrument to detect the presence of chlorine gas. When one of the fuses has its electrical connection broken, an alarm or other warning signal may be automatically generated to alert users of the installation or instrument to possible safety or control concerns that should be addressed. Thus, a possible line down situation could be avoided due to an early warning net of these fuses.

The specification describes a gas detection fuse comprising a pair of electrodes and a connecting member comprising conducting material providing an electrical connection between the pair of electrodes. The conducting material may be selected based on a gas of interest such that a chemical reaction of the gas of interest with the conducting material breaks an electrical connection between the pair of electrodes. The connecting member may comprise a fine wire of conducting material, a thin sheet or strip of conducting material, a layer of conducting material deposited (e.g., by means of vapor deposition or the like) onto a non-conducting substrate, or other suitable structure that provides a relatively high surface area for reaction with the gas.

The specification also describes an apparatus comprising an enclosure with an inlet for receiving an incoming gas flow and an outlet for discharging an outgoing gas flow, a connecting member comprising conducting material providing an electrical connection between a pair of electrodes, and a controller connected to at least one of the electrodes and configured to generate a gas warning output when the electrical connection between the pair of electrodes is broken.

The specification also describes an apparatus comprising a total organic carbon (TOC) analyzer having an exhaust that outputs gaseous analysis byproducts, a connecting member comprising conducting material providing an electrical connection between a pair of electrodes, and a controller connected to at least one of the electrodes and configured to shut down the TOC analyzer when the electrical connection between the pair of electrodes is broken.

The specification also describes an apparatus comprising a gas trap having an inlet connected to receive a gaseous exhaust and an outlet for discharging gas, and a gas detection fuse comprising a pair of electrodes and a connecting member comprising conducting material providing an electrical connection between the pair of electrodes, with the connecting member positioned at the outlet of the gas trap.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Figure 1:
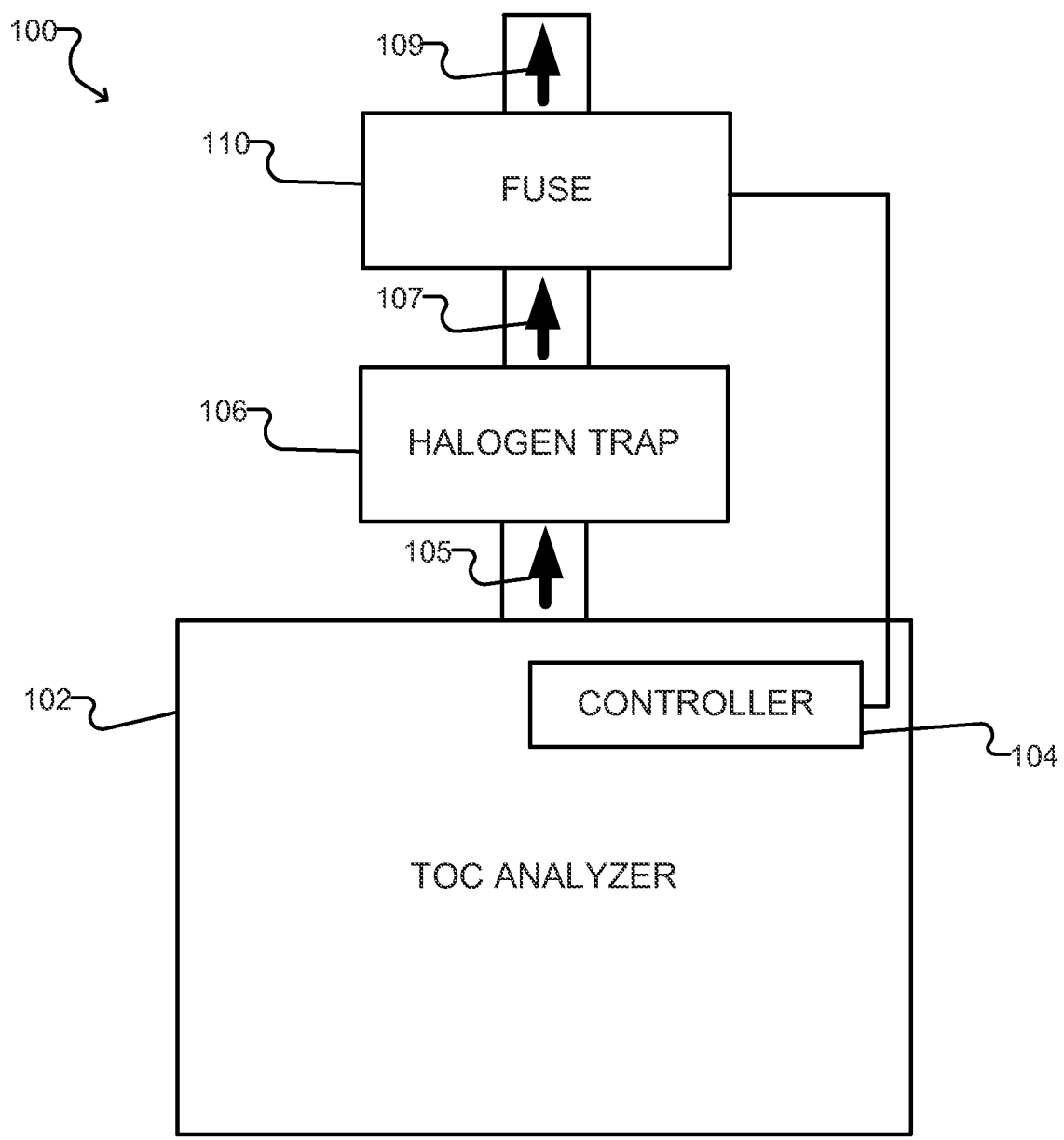
FIG. 1 is a block diagram schematically illustrating the use of a gas fuse in conjunction with a total organic carbon (TOC) analyzer according to one embodiment.

FIG. 1 shows an example system 100 including a gas detection fuse 110 according to one embodiment. The system 100 comprises a TOC analyzer 102, which may be any suitable sample analyzer as known in the art. The TOC analyzer 102 produces exhaust gasses 105 as it analyzes samples, and the exhaust gasses are directed to a halogen trap 106. The halogen trap 106 may, for example, comprise a bed of activated carbon. The halogen trap 106 normally adsorbs halogen gas such that gasses 107 exiting the trap 106 are substantially free from halogens. However, once the trap 106 has been saturated, or if the trap 106 fails, the gasses 107 may contain chlorine or other halogen gasses. After passing through the trap 106, the gasses 107 come into contact with a gas detection fuse 110, and are then exhausted through an outlet 109 to the ambient environment.

As described further below, the fuse 110 comprises a connecting member of conducting material connected between two electrodes. The conducting material is selected to react with a gas of interest such that when the gas of interest is present in the gasses 107 output from the trap 106, an electrical connection between the electrodes is broken.

For example, in some embodiments the gas of interest is chlorine and the conducting material is tin, such that when the tin is exposed to chlorine it is oxidized to produce liquid tin tetrachloride through the following reaction: $Sn(s) + 2 Cl_2(g) \rightarrow SnCl_4(l)$. The liquid tin tetrachloride fumes on contact with air and falls away thus breaking the electrical connection.

Other materials may be used in other embodiments. For example, in high condensing water environments, copper metal can be used instead of tin for the detection of Chlorine. Early prototype testing of copper connecting members in low water content environments only passivated the metal. When copper connecting members were exposed to chlorine along with high condensing water content, the metal was destroyed and the connection was broken.

The connecting member has a relatively high ratio of surface area to cross-sectional area. The connecting member may, for example, comprise a fine wire of conducting material, a thin sheet or strip of conducting material, a layer of conducting material deposited (e.g., by means of vapor deposition or the like) onto a non-conducting substrate, or other suitable structure that provides a relatively high surface area for reaction with the gas. In some embodiments, the connecting member comprises a film of conducting material with a thickness in the range of 1 to 30 microns. The specific size and shape of the connecting member may be selected based on the intended use. For example, a sheet of conducting material may be used to provide greater durability during shipment or other handling of the fuse, whereas a filament wire or the like may be prone to breakage during shipment but may be suitable for implementations where the fuse is not likely to be moved much. In general, thinner connecting members will tend to break the electrical connection sooner in the presence of a gas that is reactive with the conducting material, and as such may provide higher sensitivities and earlier warning indications than thicker connecting members.

In the illustrated embodiment the fuse 110 is operably connected to a controller 104 of the TOC analyzer 102. The controller 104 is configured to detect when the electrical connection of the fuse 110 is broken and shut down the TOC analyzer 102 in response to a broken electrical connection. As one of skill in the art will appreciate, the operative connection between the fuse 110 and the TOC analyzer 102 could be implemented in any number of ways. For example, when the electrical connection of the fuse 110 is broken, a voltage or current monitored by the controller 104 could exhibit a transition, or the supply of electrical power to the controller 104 and/or the TOC analyzer 102 could be shut off.

Figure 2:
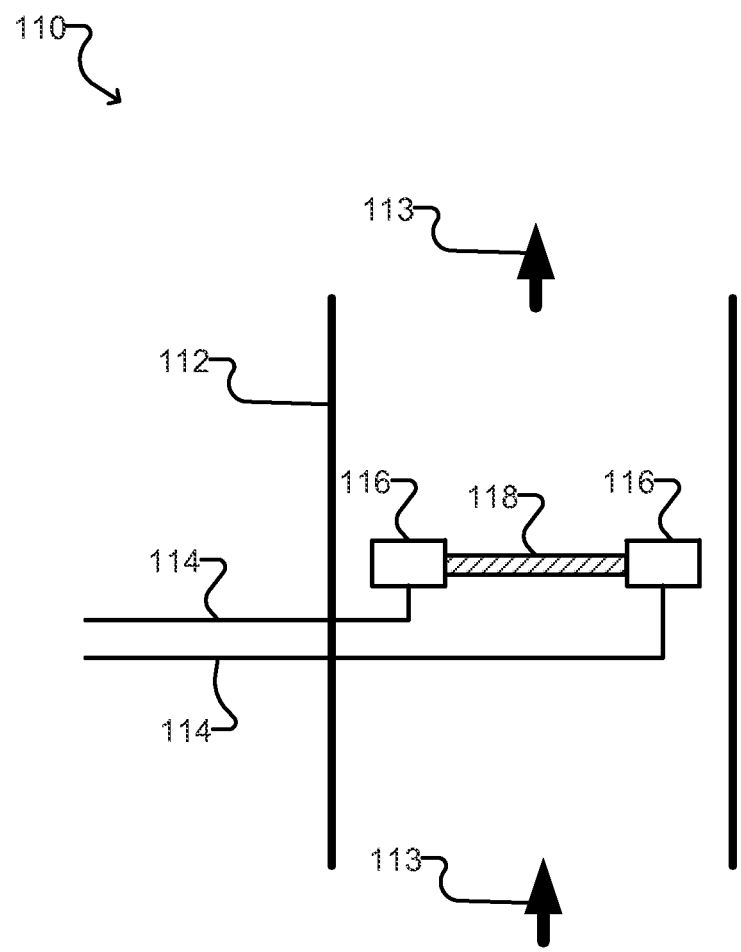
FIG. 2 schematically illustrates an example fuse according to one embodiment.

FIG. 2 shows an example gas detection fuse 110 according to one embodiment. An enclosure 112 has a flow of gas 113 passing therethrough. The enclosure 112 may, for example, be a conduit, a portion of an instrument exhaust, or any other volume through with a gas of interest may pass. A pair of leads 114 are connected to a pair of electrodes 116, and a connecting member 118 of conducting material provides an electrical connection between the electrodes. The leads 114 may be connected to a local or remote controller, which is configured to detect a break in the electrical connection between the electrodes 116. The connecting member 118 is positioned to be in contact with the flow of gas 113 in the enclosure 112. The conducting material is selected based on reactivity with one or more gasses of interest, such that when the connecting member 118 is exposed to a gas of interest, the electrical connection between the electrodes 116 is broken. In some embodiments, the leads 114 may act as the electrodes 116. For example, the leads 114 could be soldered or otherwise directly attached to the connecting member 118.

Tests were conducted on an InnovOx laboratory instrument, using test solutions of deionized water mixed with 30% NaCl wt/vol with 1% HCl and 30% Sodium Persulfate. The example tin fuses used in the tests had a thickness of 25 microns. The following table lists the time for the fuses to break when exposed to various amounts of chlorine at various concentrations:

| Tin Fuse Break times under 357 ppm Chlorine | | | | | |
|---|---|---|---|---|---|
| Test no. | Start Time | End Time | Total Time to Break | Chlorine Released (mg) | Concentration ppm per Cubic Meter |
| 1 | 10:35 | 12:12 | 97 min | 16.587 | 5.72 |
| 2 | 1:00 | 3:12 | 132 min | 22.572 | 7.78 |
| 3 | 3:52 | 5:02 | 70 min | 11.97 | 4.13 |
| 4 | 2:48 | 3:45 | 57 min | 9.747 | 3.36 |
| 5 | 10:24 | 11:56 | 92 min | 15.732 | 5.42 |
| 6 | 8:07 | 9:42 | 94 min | 16.074 | 5.54 |

The average ppm per cubic meter from the above results was 5.53 ppm. OSHA limits for Chlorine gas are 0.5 ppm for long term exposure and 1.0 ppm for short term exposure. Thus, the gas detection fuse disclosed herein would be able to shut off a TOC analyzer such as an InnovOx instrument in contact with chloride ions in a room with a volume of about 6 cubic meters or greater before enough chlorine gas accumulates to exceed OSHA limits, even if the halogen trap becomes saturated or otherwise permits chlorine to pass.

Figure 3:
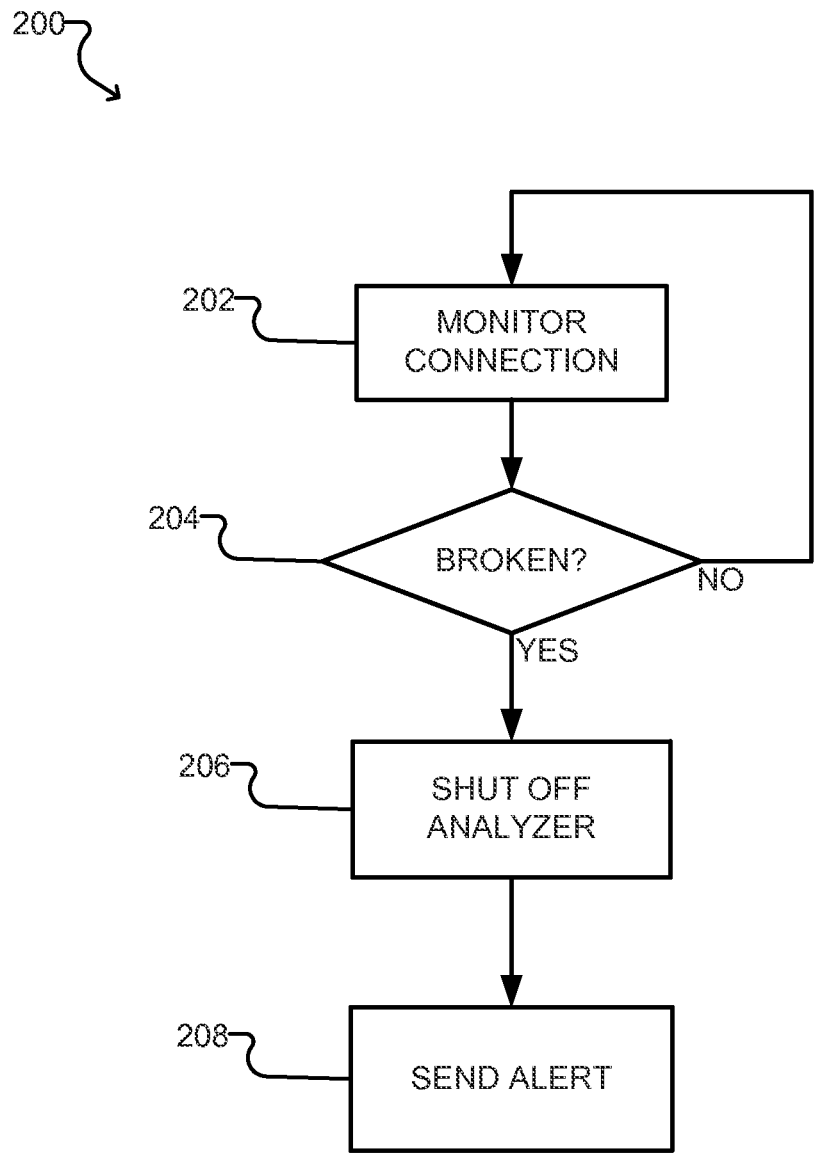
FIG. 3 is a block diagram illustrating a method of controlling a chlorine generator of a TOC analyzer according to one embodiment.

FIG. 3 is a flowchart of a method 200 for controlling an analyzer equipped with a gas detection fuse positioned to be in contact with exhaust gasses from the analyzer according to one embodiment. The electrical connection of the fuse is monitored at 202 continuously until a broken electrical connection is detected at 204. Once the electrical connection is broken, the TOC analyzer is shut off at 206. Optionally, an alert may also be sent at 208 to notify users of the TOC analyzer.

In the preceding description, for purposes of explanation, numerous details are set forth in order to provide a thorough understanding of the embodiments. However, it will be apparent to one skilled in the art that these specific details are not required. In other instances, well-known electrical structures and circuits are shown in block diagram form in order not to obscure the understanding. For example, specific details are not provided as to whether the embodiments described herein are implemented as a software routine, hardware circuit, firmware, or a combination thereof.

Embodiments of the disclosure can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

What is claimed is:

1. A gas detection fuse, comprising:
    a pair of electrodes; and
    a connecting member coupled to the pair of electrodes, the connecting member comprising a tin conducting material in electrical communication with the pair of electrodes, wherein the tin conducting material is reactable with chorine gas to produce liquid tin tetrachloride and thereby break the electrical communication between the pair of electrodes.

2. The gas detection fuse of claim 1 wherein the connecting member comprises a sheet of conducting material having a thickness between about 1 and 30 microns.

3. The gas detection fuse of claim 1 wherein the connecting member comprises a filament wire of conducting material.

4. The gas detection fuse of claim 1 wherein the connecting member comprises a layer of conducting material deposited on a non-conductive substrate.

5. The gas detection fuse of claim 4, wherein the pair of electrodes are monolayered.

6. The gas detection fuse of claim 1 wherein the pair of electrodes and the connecting member are mounted on a circuit board.

7. The gas detection fuse of claim 1 wherein the connecting member is positioned in a gas conduit.

8. The gas detection fuse of claim 1 further comprising a controller and an alarm, wherein the controller is connected to at least one of the electrodes and the alarm, wherein the controller is configured to generate an alarm signal in response to determining that the electrical communication between the pair of electrodes is broken.

9. A gas trap comprising:
    an inlet to receive a gas from a total organic carbon analyzer;
    an outlet for discharging any of the gas that escapes the gas trap; and
    the gas detection fuse of claim 1, wherein the connecting member is positioned in communication with the outlet.

10. An apparatus comprising:
    an enclosure with an inlet for receiving an incoming gas flow and an outlet for discharging an outgoing gas flow;
    the gas detection fuse of claim 1 positioned in the enclosure between the inlet and the outlet; and
    a controller connected to at least one of the electrodes and configured to generate a gas warning output when the electrical connection between the pair of electrodes is broken.

11. An apparatus comprising:
    a total organic carbon (TOC) analyzer having an exhaust that outputs gaseous analysis byproducts;
    the gas detection fuse of claim 1 positioned to contact the gaseous analysis byproducts; and
    a controller connected to at least one of the electrodes and configured to shut down the TOC analyzer when the electrical connection between the pair of electrodes is broken.

12. The apparatus of claim 11 further comprising a gas trap having an inlet connected to the exhaust of the TOC analyzer, and an outlet for discharging gas, wherein the connecting member is positioned at the outlet of the gas trap.

* * * * *